United States Patent [19]

Sørensen et al.

[11] Patent Number: 5,849,704
[45] Date of Patent: Dec. 15, 1998

[54] PHARMACEUTICAL FORMULATION

[75] Inventors: Hans Holmegaard Sørensen, Virum; Lars Skriver, Vedæk; Annie Rassing Hoelgaard, Holte, all of Denmark

[73] Assignee: Novo Nordisk A/S, Bagsvaerd, Denmark

[21] Appl. No.: 458,386

[22] Filed: Jun. 2, 1995

Related U.S. Application Data

[63] Continuation-in-part of Ser. No. 12,817, Feb. 3, 1993, which is a continuation-in-part of Ser. No. 827,200, filed as PCT/DK92/00379 Dec. 16, 1992, published as WO93/12812 Jul. 8, 1993.

[30] Foreign Application Priority Data

Dec. 20, 1991 [DK] Denmark .................... 2046/91
Nov. 10, 1992 [DK] Denmark .................... 1364/92

[51] Int. Cl.$^6$ .................... A61K 37/02; A61K 47/10; A61K 47/26
[52] U.S. Cl. .................... 514/12; 514/21; 530/362; 530/363; 530/397; 530/399
[58] Field of Search .................... 514/12, 21; 530/399, 530/397, 362, 363

[56] References Cited

U.S. PATENT DOCUMENTS

| | | | |
|---|---|---|---|
| 2,174,862 | 10/1939 | Sayhon | 514/12 |
| 4,816,568 | 3/1989 | Hamilton, Jr. et al. | 514/2 |
| 4,917,685 | 4/1990 | Viswanathan et al. | 604/891.1 |

FOREIGN PATENT DOCUMENTS

| | | |
|---|---|---|
| 0 303 746 A1 | 8/1987 | European Pat. Off. . |
| 0 374 120 A2 | 12/1989 | European Pat. Off. . |
| WO 89/09614 | 10/1989 | WIPO . |
| 93/12812 | 7/1993 | WIPO . |
| 93/12811 | 8/1993 | WIPO . |
| 93/19776 | 10/1993 | WIPO . |
| 94/03198 | 2/1994 | WIPO . |

OTHER PUBLICATIONS

Remingtons Pharmaceutical Sciences, 16th ed. Arthur Osai ed., Mack Publishing Co., Easton, PA. 11980 p. 1535.
Yu–Chang et al., J. Parent. Sci. & Tech., vol. 42, pp. S3–S26 (1988).
Manning et al., Pharmaceutical Research, vol. 6, No. 11, pp. 903–918 (1989).
Johnson et al., The Journal of Biological Chemistry, vol. 264, No. 24, pp. 14262–14271 (1989).
Liew–Cheng Teh et al., J. of Biol. Chem., vol. 262, No. 14, pp. 6472–6477 (1987).
Becker et al., Biotech. and App. Biochem., vol. 10, pp. 326–337 (1988).
Houghten et al., Arch. of Biochem. Biophysics, vol. 178, pp. 350–355 (1977).
Riggen et al., Analytical Biochem., vol. 167, pp. 199–209 (1987).
Gellerfors et al., Acta Pædiatr Scand [Suppl], vol. 370, pp. 93–100 (1990).
Kaufman, Pharmaceutical Research, vol. 7. No. 3, pp. 289–292 (1990).
Becker et al., Biotech. and Applied Biochem., vol. 10, pp. 478–487 (1987).
M. J. Kaufman, Pharmaceutical Research., vol. 7, No. 3, pp. 289–293, 1990.
Teh et al, The J. of Biological Chem., vol. 262, No. 14, pp. 6472–6477, 1987.
Wang et al., J. of Parenteral Science and Technology, vol. 42, pp. S3–S27, 1988.
Jensen et al., Biotech. and Bioengineering, vol. 36, No. 1, pp. 1–11, 1990.

*Primary Examiner*—Howard E. Schain
*Assistant Examiner*—Lynn Touzeau
*Attorney, Agent, or Firm*—Steve T. Zelson; Cheryl H. Argis

[57] ABSTRACT

A pharmaceutical preparation comprising a growth hormone and histidine or a derivative of histidine as additive or buffering substance shows a very high stability against deamidation, oxidation and cleavage of peptide bonds. The stability of the product allows for the storing and shipment thereof in a lyophilized state or in the form of a dissolved or re-dissolved preparation at ambient temperature. Crystallization of growth hormone in the presence of histidine or a derivative thereof gives rise to a higher yield of crystals having a higher purity than known methods.

21 Claims, 2 Drawing Sheets

PHARMACEUTICAL FORMULATION

This application is a continuation-in-part of U.S. patent application Ser. No. 08/012,817, filed Feb. 3, 1993 which is a continuation-in-part of U.S. patent application Ser. No. 07/827,200, filed as PCT/DK92/00379 Dec. 16, 1992, published as WO93/12812 Jul. 8, 1993.

FIELD OF THE INVENTION

The present invention relates to a stabilized pharmaceutical composition(s) comprising growth hormone, crystalline growth hormone comprising histidine or a derivative thereof, and a method of preparing such crystals.

BACKGROUND OF THE INVENTION

The growth hormones (GH) from man and from the common domestic animals are proteins of approximately 191 amino acids, synthesized and secreted from the anterior lope of the pituitary gland. Human growth hormone consists of 191 amino acids.

Growth hormone is a key hormone involved in the regulation of not only somatic growth, but also in the regulation of metabolism of proteins, carbohydrates and lipids. The major effect of growth hormone is to promote growth.

The organ systems affected by growth hormone include the skeleton, connective tissue, muscles, and viscera such as liver, intestine, and kidneys.

Until the development of the recombinant technology and the cloning of the growth hormone gene now giving rise to production of e.g. human growth hormone (hGH) and Met-hGH in industrial scale, human growth hormone could only be obtained by extraction from the pituitary glands of human cadavers. The very limited supplies of growth hormone restricted the use thereof to longitudinal growth promotion in childhood and puberty for treatment of dwarfism, even though it has been proposed for inter alia treatment of short stature (due to growth hormone deficiency, normal short stature and Turner syndrome), growth hormone deficiency in adults, infertility, treatment of burns, wound healing, dystrophy, bone knitting, osteoporosis, diffuse gastric bleeding, and pseudoarthrosis. Furthermore, growth hormone has been proposed for increasing the rate of growth of domestic animals or for decreasing the proportion of fat in animals to be slaughtered for human consumption.

Pharmaceutical Compositions of Growth Hormone

Pharmaceutical preparations of growth hormone tend to be unstable. Degradation products such as deamidated or sulfoxylated products and diner or polymer forms are generated—especially in solutions of growth hormone.

The predominant degradation reactions of hGH are 1) deamidation by direct hydrolysis or via a cyclic succinimide intermediate to form various amounts of L-asp-hGH, L-iso-asp-hGH, D-asp-hGH, and D-iso-asp-hGH (Wang and Hanson, 1988, J. Parenteral Science and Technology 42 (Suppl.) 53–525; Manning et al., 1989, Pharmaceutical Research 6 (11) 903–918; and Johnson et al., 1989, J. Biol. Chem. 264:1462–1471); 2) oxidation of the methionine residues in positions 14 and 125 (Teh et al., 1987, J. Biol. Chem. 262:785–794; Becker et al., 1988, Biotech. Appl. Biochem. 10:326–337; Houghten et al., 1977, Arch. Biochem. Biophys. 178:350–355; Riggin et al., 1987, Anal. Biochem. 167:199–209; Gellerfors et al., 1990, Acta Paediatr. Scand (suppl), 370:93–100; and Kaufman, 1990, Pharm. Res., 7 (3) 289–292); and 3) cleavage of peptide bonds. Deamidation especially takes place at the Asn in position 149. hGH is rather easily oxidized in positions 14 and 125, especially in solution (Teh et al., 1987, J. Biol. Chem. 262:785–794; Becker et al., 1988, Biotech. Appl. Biochem. 10:326–337; Houghten et al., 1977, Arch. Biochem. Biophys. 178:350–355; Riggin et al., 1987, Anal. Biochem. 167:199–209).

The oxidation of hGH in solution forming sulfoxides is normally due to the oxygen dissolved in the preparation. The solubility of oxygen in distilled water is about 200 $\mu$M (Kaufman, 1990, Pharm. Res., 7 (3) 289–292). As the concentration of hGH in a preparation comprising 4 IU/ml is 1.3 mg/ml corresponding to 60 nM hGH, oxygen will, at normal storing conditions, be present in an excess of about 3000 times the stoichiometric amount for oxidation of hGH. It is not feasible to try to solve the problem by degassing of buffers before tapping and packing the preparations.

At present, it is not believed that these degradation products should have toxic or altered biological activity or receptor binding properties. However, there are indications that the conformation stability of the sulfoxides is reduced as compared to native hGH.

For the development of a stable, dissolved preparation comprising hGH, it is of importance to know the rate of formation of sulfoxides as well as means to control the oxidation.

The kinetics of degradation depend on temperature, pH and various additives or adjuvants in the hGH formulation.

Due to the instability, growth hormone is, at present, lyophilized and stored in the lyophilized form at 4° C. until it is reconstituted for use in order to minimize the degradation.

The lyophilized pharmaceutical preparations comprising hGH are, at present, reconstituted by the patient and then stored at a low temperature, often at about 4° C. in the refrigerator as a solution during the period of use of up to 14 days, during which some degradation will take place.

However, the process of reconstitution of the lyophilized growth hormone tends to provide difficulties for the patient. Thus, it is at present preferred to reconstitute the growth hormone as late as possible before use and to store and ship the preparation in a lyophilized state. The chain from the manufacturer to the pharmacy is apt for handling the preparations at a controlled low temperature of e.g. 4° C. which allows for a long shelf life of up to two years.

However, the extended use of pen systems for self-medication and the expanded field of use calls for a preparation which is stable for a sufficient time with the end user under conditions where "sufficient" cooling is not always available. Preferably, a preparation should be stable with the end user in a lyophilized state for about one month and additionally for one month in a reconstituted state in a pen device for the intended period of use of a cartridge.

International Patent Publication No. WO 89/09614 and Australian patent application No. 30771/89 disclose a stable pharmaceutical formulation containing human growth hormone, glycine, and mannitol. Such a preparation shows improved stability during normal processing and storage in a lyophilized state as well as in the period of use after the reconstitution.

U.S. Pat. No. 4,876,568, discloses that animal growth hormone may be stabilized with various stabilizers to give decreased formation of insolubles and preservation of the soluble activity in aqueous environments. Such stabilizers including certain polyols, amino acids, polymers of amino acids having a charged side group at physiological pH, and choline salts. Polyols are selected from the group consisting of non-reducing sugars, sugar alcohols, sugar acids, pentaerythritol, lactose, water-soluble dextrans and Ficoll; amino acids are selected from the group consisting of glycine, sarcosine, lysine or salts thereof, serine, arginine or salts thereof, betaine, N,N,-dimethyl-glycine, aspartic acid or salts thereof, glutamic acid or salts thereof; a polymer of an amino acid having a charged side group at physiological pH may be selected from polylysine, polyaspartic acid, polyglutamic acid, polyarginine, polyhistidine, polyornithine and salts thereof; and choline derivatives are selected from the group consisting of choline chloride, choline dihydrogen citrate, choline bitartrate, choline bicarbonate, tricholine citrate, choline ascorbate, choline borate, choline gluconate, choline phosphate, di(choline)sulphate and dicholine mucate. U.S. Pat. No. 4,876,568 notes that polyhistidine can be used as a potential stabilizer for animal growth hormone but there is no indication whether it stabilizes an animal growth hormone or human growth hormone. Furthermore, U.S. Pat. No. 4,876,568 mentions that poly-DL-lysine HBr is preferred.

EP 374120 discloses a stabilized preparation of growth hormone comprising a buffered polyol excipient comprising a polyol having three hydroxy groups and a buffer to achieve a pH in a range in which the growth hormone retains its bioactivity for a sufficient period of time. Histidine is mentioned as a buffer for a polyol having three hydroxy groups. Specifically, EP 374120 teaches that histidine hydrochloride may be used as a buffer for buffering a polyol having three hydroxy groups for improving the stability of a growth hormone preparation in the form of a solution comprising a high concentration of growth hormone and a polyol as stabilizer. Furthermore, histidine hydrochloride must be added in an amount of about 3% by weight of the solution corresponding to a concentration of ~0.15M solution of histidine hydrochloride. EP 374120 also teaches that histidine alone does not impart chemical and physical stability to a growth hormone preparation.

Crystallization of Growth Hormone

Although readily available in quantities sufficient for crystallization, no successful crystallization of GH has been reported so far. Micro crystals, or amorphous material have been reported from a variety of sources: (Jones et al., 1987, Bio-Technology 5:499–500; Wilhelmi et al., 1984, J. Biol. Chem. 176:735–745; Clarkson et al., 1989, J. Mol. Biol. 208:719–721; and Bell et al., 1985, J. Biol. Chem. 260:8520–8525).

The hanging drop method is the most common method used in attempts for crystallizing growth hormone. Apparently due to the heterogenicity of growth hormone preparations, the size and the shape of the crystals reported varied significantly. The largest crystals have been reported by Jones et al., 1987, BioTechnology 5:499–500. For their successful experiments, they used a mixture of polyethylene glycol 3500 and beta octyl glucoside at neutral pH. Clarkson et al., 1989, J. Mol. Biol. 208:719–721 reported that the use of lower alcohols and acetone permitted the generation of crystals of 0.001 to 0.005 cubic mm with varying shapes. None of the known methods are however suitable for commercial production of growth hormone crystals a.o. due to the fact that periods of growth of from several weeks up to one year are needed.

Bovine growth hormone has been formulated for veterinarian use in a mixture of divalent ions and an oil (EP 343696). By addition of $ZnCl_2$ to either bovine or porcine growth hormone in the presence of lipids undefined particles were produced to form a prolonged release formulation. The growth hormone was dispersed in the carrier in such a way as to trap 1 to 4 Zn molecules per growth hormone molecule. The solutions were prepared in the presence of varying concentrations of denaturing solutes (1 to 4M of urea) at high pH (9.5). A reproduction of this process with hGH has shown that it is not possible to produce crystals in this way. No crystals were formed when carrying out the method using human growth hormone instead of bovine growth hormone as disclosed in EP 343696. Only an amorphous precipitate could be recovered.

From the literature it is well known that the presence of divalent cations during the process of crystallization of insulin permits not only excellent orientation during analysis, but also improved physical conditions for the crystallization (see e.g. U.S. Pat. No. 2,174,862). However, with the exception of results reported in EP 343696, there is no indication that the presence of divalent cations would assist in obtaining homogeneous growth hormone crystals when the method described in EP 343696 is carried out in attempts to crystallize human growth hormone.

OBJECTS OF THE INVENTION

Thus, there is a need for more stable compositions of growth hormone being stable in a lyophilized state at a relative high temperature for a period and additionally for a period of use at a relatively high temperature in solution. Such stabilization is of very great importance when moving the administration of the growth hormone from clinics to the homes of the individuals to be treated where optimal storage may not be available as indicated above.

Furthermore, the shift in pattern of administration of growth hormone to the use of pen devices calls for a stable dissolved composition comprising growth hormone in order to facilitate the handling to be performed by the patient. Crystalline growth hormone would be very soluble. Thus, it is an object of the invention to obtain homogeneous preparations of crystalline growth hormone in high yield.

Furthermore, it is an object of this invention to produce a stable dissolved composition comprising growth hormone ready to use in the form of cartridges fitting into the pen device used by the patient who may then avoid the reconstitution of the preparation and, hence, will not have to be in the possession of a lyophilized preparation, a suitable vehicle for reconstitution as well as the necessary skill and sterile equipment for sterile reconstitution of the preparation. For safety reasons, it will also be desirable to avoid the reconstitution of a lyophilized preparation just before the use of the preparation.

Furthermore, it would also be an advantage to avoid the lyophilization step in the production of growth hormone preparations. Lyophilization is a time consuming and costly process and is also often a "bottleneck" in the production due to the limited capacity of the freeze drier.

Thus, there is a need to reduce the rate of the degradation processes in order to allow for dissolved hGH preparations being stable during shelf life and during the period of use of up to one month.

SUMMARY OF THE INVENTION

The invention is directed to a pharmaceutical composition of human growth hormone or derivative thereof comprising only histidine or a derivative thereof as additive or buffering substance in an amount of from about 0.1 to about 12 mg histidine or derivative thereof per mg of growth hormone. It has now surprisingly been found that such a composition shows a very high stability against deamidation, oxidation and cleavage of peptide bonds. The stability of the product allows for the storing and shipment thereof in a lyophilized state or in the form of a dissolved or redissolved preparation.

A further, preferred embodiment of the invention is in the form of a pharmaceutical composition of human growth hormone comprising histidine or a derivative thereof in the form of a buffered aqueous suspension of crystals of growth hormone buffered with histidine buffer. In a most preferred embodiment, the histidine buffer has a concentration from about 1 mM to about 100 mM. Such a composition is very stable and keeps the growth hormone in a crystalline phase during the storing and shipment in a ready-to-use form giving an even lower tendency to degrade and acts like a dissolved preparation when injected, i.e. there is no sustained release of the human growth hormone.

Another way of stabilizing growth hormone according to the invention is to form crystals of growth hormone giving a good protection against degradation. It has surprisingly been found that preparations of growth hormone in the form of crystals comprising histidine fulfill the above-mentioned needs. The crystals in dried form may be used directly as a growth hormone preparation to be reconstituted before use in the conventional manner.

Thus, the present invention also relates to crystalline growth hormone or a derivative thereof comprising histidine or a derivative thereof and an organic or inorganic cation. As will be disclosed in the examples herein, the quality of such crystals is better than the quality obtained using previous formulations.

As noted in the previous section, supra, it is well known that the presence of divalent cations during the process of crystallization of insulin permits not only excellent orientation during analysis, but also improved physical conditions for the crystallization (see e.g. U.S. Pat. No. 2,174,862). Growth hormone is, however, more than three times larger than insulin and has a totally different conformation. Surprisingly it has now been shown that the addition of cations to solutions containing hGH or a derivative thereof and histidine or a derivative thereof renders possible the generation of stable, uniform crystals of the growth hormone in high yields. Furthermore, the period of time necessary for the formation of high quality crystals of hGH is relatively short.

A further aspect of the invention is a method for preparing crystals of growth hormone and histidine or a derivative of histidine comprising the steps of:
 a) forming a solution of growth hormone or growth hormone derivative in a solvent and adding histidine or a derivative of histidine and optionally adjusting the pH to a value from about 5 to about 8 using hydrochloric acid;
 b) adding organic or inorganic cations to the solution of step (a);
 c) crystallizing the solution of step (b) at a temperature from about 0° C. to about 30° C.; and
 d) isolating the crystals formed in step (c).

The invention is further directed to a method of treatment of a disorder associated with growth hormone deficiency comprising treating a patient with an effective amount of the pharmaceutical compositions or crystalline growth hormone of the present invention.

DETAILED DESCRIPTION OF THE INVENTION

Figure 1:
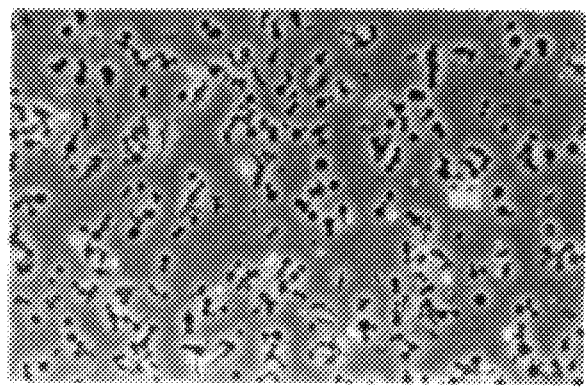
FIG. 1 shows a photo of crystals prepared without addition of histidine, specifically, hGH crystals formed in the presence of phosphate buffer. Magnification: 400×.

The present invention is directed to a pharmaceutical composition comprising growth hormone or a derivative thereof and histidine as a buffering substance. The invention is further directed to crystalline growth hormone or a derivative thereof comprising histidine or a derivative thereof as well as a method for making such a crystalline growth hormone.

Pharmaceutical Compositions

The pharmaceutical compositions of the invention may be formulated for administration in any suitable way, e.g. by parenteral or oral administration or administration to a mucosal membrane, e.g. nasal administration. The pharmaceutical formulation may be presented in the form of a dose in a vial or cartridge or any other suitable container such as a prefilled syringe or a pen device.

In one embodiment, the composition comprises human growth hormone or a derivative thereof and histidine or a derivative thereof as additive or buffering substance in an amount of from about 0.1 to about 12 mg histidine or derivative thereof per mg of growth hormone. In a specific embodiment of the invention, the histidine has a concentration from about 1 mM to about 100 mM, more preferred in an amount from about 1 to about 10 mM, preferably from about 2 to about 6 mM, most preferred about 3–5 mM. The growth hormone may be in solid form or may be in a buffer solution, e.g., histidine, citrate, tartrate or phosphate buffer.

In the present context, "growth hormone" may be growth hormone from any origin such as avian, bovine, equine, human, ovine, porcine, salmon, trout or tuna growth hormone, preferably bovine, human or porcine growth hormone, human growth hormone being most preferred. The growth hormone used in accordance with the invention may be native growth hormone isolated from a natural source, e.g. by extracting pituitary glands in a conventional manner, or a growth hormone produced by recombinant techniques, e.g. as described in E. B. Jensen and S. Carlsen in Biotech and Bioeng. 36, 1–11 (1990). The "growth hormone derivative" may be a truncated form of growth hormone wherein one or more amino acid residues has (have) been deleted; an analog thereof wherein one or more amino acid residues in the native molecule has (have) been substituted by another amino acid residue, preferably the residue of a naturally occurring amino acid, as long as the substitution does not have any adverse effect such as antigenicity or reduced action; or a derivative thereof, e.g. deamidated or sulfoxidated forms of the growth hormone or forms having an N- or C-terminal extension such as Met-hGH, Met—Glu—Ala—Glu-hGH or Ala—Glu-hGH. The preferred growth hormone is human growth hormone.

The term "dose" of growth hormone refers to that amount that provides therapeutic effect in an administration regimen. The compositions hereof are prepared containing amounts of hGH at least about 0.1 mg/ml, preferably upwards of about 10 mg/ml, preferably from about 1 mg/ml to about 40 mg/ml, more preferably from about 1 mg/ml to about 25 mg/ml, e.g. from 1 mg/ml to about 5 mg/ml, calculated on the ready-to-use formulation. For use of these compositions in administration to human beings suffering from hypopituitary dwarfism, for example, these formulations contain from about 0.1 mg/ml to about 10 mg/ml, corresponding to the currently contemplated dosage regimen for the intended treatment. The concentration range is not critical to the invention and may be varied by the physician supervising the administration.

The term "derivatives of histidine" is used, for the present purpose, to designate amides and esters of histidine such as the methyl or ethyl ester, dipeptides such as His—Gly, His—Ala, His—Leu, His—Lys, His—Ser, and His—Phe, and analogs or derivatives of His such as imidazole, desamino-His or poly-His. For the sake of simplicity, the contents of histidine or a derivative thereof in the compositions of the invention is calculated using the molar weight of histidine itself. The histidine may be 1- or d-histidine or mixture thereof.

A preferred embodiment of the invention is in the form of a pharmaceutical composition of human growth hormone comprising histidine or a derivative thereof in the form of a buffered aqueous solution of growth hormone buffered with histidine buffer having a concentration from about 1 mM to about 100 mM. Such preparation is in a ready-to-use form and may be stored and shipped as an aqueous solution without any considerable degradation. L-histidine has a pKA of 6.0 and is, accordingly suitable as a buffer itself at pH 6.5. The formulation of histidine at pH 6.5 is considered stable at 25° C. for almost 50 days.

For stability reasons, the pH of a solution or suspension composition is preferably adjusted to a value in the interval from about 2 to about 8. Preparations having a pH from about 5 to about 7 and especially a pH at about 6.8 are more preferred. The pH adjustment can be made with a physiologically acceptable acid, e.g., mineral acid such as HCl, sulphuric acid or nitric acid or an organic acid such as acetic acid.

The pharmaceutical compositions of the invention may furthermore comprise salts for adjusting the tonicity and/or an excipient in order to facilitate the processing thereof, e.g. lyophilization and the rapid and complete dissolution of a lyophilized formulation when reconstituting the formulation before use. The term "salts" is used to designate additional agents for facilitating the processing or reconstitution of pharmaceutical preparations comprises conventional additives such as alkaline metal, alkaline earth metal or ammonium salts of organic acids such as citric acid, tartaric acid or acetic acid, e.g. sodium citrate, sodium tartrate or sodium acetate, or of mineral acids such as hydrochloric acid, e.g. sodium chloride. An excipient may be selected from disaccharides such as lactose, trehalose, and sucrose, sugar alcohols such as sorbitol or mannitol, polysaccharides such as the polymers commercialized as Dextran® products such as Dextran® 40, Dextran® 70 or Dextran® 75, and Ficoll® and polyvalent alcohols such as polyethylene glycol or polyvinyl alcohol or a combination of two or more of these.

In the present context "high stability" is obtained when the formulation is more stable than the conventional formulation comprising phosphate buffer and preferably as stable as a corresponding formulation comprising histidine as stabilizer in which the de-amidation of hGH is reduced by approximately 20% as compared with phosphate buffer as disclosed in WO 93/12812.

The solvent used in the compositions of the invention may be water, alcohols such as ethyl, n-propyl or isopropyl, butyl alcohol or mixtures thereof. The solvent may comprise a preservative such as m-cresol or benzyl alcohol.

The compositions of the invention may also be in the form of a lyophilized powder or "cake" comprising growth hormone or a growth hormone derivative, and histidine or a derivative thereof in an amount from about 0.1 to about 12 mg histidine or derivative thereof per mg growth hormone or growth hormone derivative and a bulking agent for lyophilization selected from the group consisting of sugar alcohols and disaccharides and mixtures thereof. A "sugar alcohol" may e.g. be mannitol, xylitol, erythritol, threitol, sorbitol or glycerol. In a preferred embodiment, the sugar alcohol is mannitol. In the present context "disaccharide" is used to designate naturally occurring disaccharides such as sucrose, trehalose, maltose, lactose, sepharose, turanose, laminaribiose, isomaltose, gentiobiose or melibiose.

Lyophilized compositions according to the invention comprising sucrose are preferred due to a very high stability and compositions comprising sucrose and mannitol are especially preferred combining very high stability with a very good processability giving firm lyophilized products being readily dissolvable and very stable in solution for an extended period of time after dissolution. In the present context, "high stability" is obtained when the preparation is more stable than the conventional formulations comprising phosphate buffer. Further preferred compositions according to the invention are preparations comprising mannitol and trehalose as bulking agent for the lyophilization. Compositions according to the invention comprising mannitol and a disaccharide normally comprises about equal amount of the two constituents on a weight basis.

The amount of sucrose present in the compositions of the invention may vary within wide limits. The ratio of growth hormone to sucrose may vary from about 0.005 to about 1.5 on a weight basis. Thus, the amount of sucrose may be from about 0.67 to about 200 mg per mg of growth hormone, an amount of from about 1.1 to about 50 mg per mg of growth hormone being preferred.

Lyophilization of hGH in histidine buffer does not give rise to any problems. The rate of deamidation is reduced by 20% on standing after redissolving as compared to phosphate buffer.

Crystalline Growth Hormone

Crystals of growth hormone or a derivative thereof and histidine or a derivative of histidine may be prepared by a method comprising the steps of:

a) forming a solution of growth hormone or growth hormone derivative in a solvent and adding histidine or a derivative of histidine and optionally adjusting the pH to a value from about 5 to about 8 using hydrochloric acid;

b) adding organic or inorganic cations to the solution of step (a);

c) crystallizing the solution of step (b) at a temperature from about 0° C. to about 30° C.; and d) isolating the crystals formed in step (c).

It has been found that crystallizing hGH in the presence of histidine or a derivative thereof gives a higher yield of crystalline hGH in the form of bigger and more pure and uniform crystals then crystallization in the presence of phosphate buffer normally used for formulation of preparations of hGH.

Thus, the isolation and purification of the crystals is facilitated.

The yield of crystals has been increased by ~20% when carrying out the crystallization in the presence of histidine as compared with crystallizing from previous formulations.

The starting material, the growth hormone, may be a concentrate obtained directly from the fermentation broth or a conventional lyophilized preparation which is dissolved in the solvent and adjusted to a concentration of preferably more than about 0.1 mg/ml, preferably a concentration from about 4 to about 7 mg/ml and most preferred a concentration of about 6 mg/ml. The solvent used in step a) is suitably an aqueous buffer such as phosphate buffer or histidine buffer.

The crystallization is allowed to proceed for a period from about 1 to about 120 hours, preferably from about 5 to about 72 hours and most preferred from about 20 to about 48 hours at a temperature. The temperature is preferably from about 4° to about 25° C.

The pH in step a) is normally from about 5.0 to about 7.5, preferably from about 5.0 to about 6.8, more preferred from about 5.8 to about 6.5, and most preferred from about 6.0 to about 6.3.

The concentration of histidine or histidine derivative in step a) may vary from about 5 to about 25 mM, about 5 to about 15 mM being preferred, in order to have crystals of appropriate size and quality as stated above.

Divalent cations are preferred and inorganic cations such as Zn++ has been found to be well suited for the fast formation of stable growth hormone crystals. Also, mixtures of cations can be used.

The cation should be added in an amount providing fast and efficient formation of well defined crystals. The upper limit for the amount of added cation is the amount which would cause unspecific precipitation of substantial amounts of amorphous material.

When using $Zn^{++}$, suitable concentrations will typically be from about 0.2 to 10 mol $Zn^{++}$/mol growth hormone. However, if the crystallization reaction mixture contains a buffer or other compound which is capable of binding the cation, e.g. in a complexed form, a higher added concentration of the cation will be needed for the crystallization process in order to compensate for this binding.

$Zn^{++}$ will preferably be used in an amount which will cause formation of growth hormone crystals having a molar ratio between $Zn^{++}$ and growth hormone from about 0.2 to about 10, more preferred from about 0.5 to about 5 and preferably from about 0.5 to about 2.

When using other inorganic cations, the concentration may be varied between 0.5 and 10 mol cation/mol growth hormone.

In a preferred embodiment of the invention, an organic solvent or a mixture of organic solvents is added in step a). Suitable organic solvents to be added for the crystallization may be chosen from short chained aliphatic, alicyclic or aromatic alcohols and ketones such as methanol, ethanol, 1- and 2-propanol, cyclohexanol, acetone, and phenol or m-cresol. Preferred organic solvents are ethanol and acetone, ethanol being most preferred. The concentration of the organic solvent may be from about 0.1 to about 50% v/v, preferably from about 0.1 to about 30%, more preferably from about 0.1 to about 20%, even more preferably from about 5 to about 15% and most preferred from about 6 to about 12% v/v.

The solution may be seeded by adding small and well defined crystals of hGH of hexagonal or needle shape, but preferably no seeding is carried out.

The present process may be used as a fast and efficient downstream processing of the growth hormone in question, due to the formation of crystals in large volumes of solutions.

When using ethanol as the organic solvent, the concentration is suitably between about 0.1 and about 20%, more preferably between 5 and 15% and preferably from about 6 to about 12% (v/v).

The crystals formed may be isolated by conventional methods, such as centrifugation or filtration, washing and optionally lyophilization to remove traces of organic solvents.

The size of the crystals will be dependent on the $Zn^{++}$ to growth hormone ratio and the choice and content of solvent used in the process.

hGH crystals according to the present invention have been shown to have a biological potency similar to that of a solubilized hGH standard in in vitro tests. The novel growth hormone crystals can thus be used for the same indications as the commercially available hGH preparation.

The invention is further illustrated in the following examples which are not in any way intended to limit the scope of the invention as claimed.

EXPERIMENTAL PART

Example 1

Reduction of the deamidation.

The rate of deamidation was examined at 37° C. for hGH preparations comprising 4 IU and 12 IU at pH 6.5 in His buffer as compared to phosphate buffer at the same pH.

The hGH preparation comprising 4 IU having the composition A was prepared by dissolving 13.3 mg hGH in 10 ml 10 mM histidine buffer prepared by dissolving 15.5 mg histidine in 10 ml deionized water containing 0.9% benzyl alcohol and adding 0.1 N hydrochloric acid to pH 6.5. The preparation comprising 12 IU was prepared by dissolving 40 mg hGH in the same constituents as stated above.

The hGH preparation comprising 4 IU having the composition B was prepared by dissolving 13.3 mg hGH in 10 ml 10 mM disodium phosphate prepared by dissolving 17.8 mg disodium-hydrogen-phosphate in 10 ml deionized water, containing 0.9% (v/v) of benzyl alcohol and adding 0.1 N phosphoric acid to pH 6.5. The preparation comprising 12 IU was prepared by dissolving 40 mg hGH in the same constituents as stated above.

Composition A:
10 mM His
0.9% benzyl alcohol
HCl at pH 6.5
Composition B:
10 mM disodium phosphate
0.9% benzyl alcohol
phosphoric acid at pH 6.5

The preparations were examined by IE-HPLC for the contents of desamido-hGH immediately after the reconstitution and after 7 days at 37° C. The results are shown in Table 1, infra.

TABLE 1

|  | Deamidation. | |
| --- | --- | --- |
|  | Preparation % | Desamido |
| Buffer A | 4 IU/ml | 1.7 |
| Start | 12 IU/ml | 2.1 |
| Buffer A | 4 IU/ml | 10.1 |
| 7 days at 37° C. | 12 IU/ml | 10.4 |
| Buffer B | 4 IU/ml | 1.8 |
| Start | 12 IU/ml | 2.3 |
| Buffer B | 4 IU/ml | 16.9 |
| 7 days at 37° C. | 12 IU/ml | 14.9 |

From the above figures, it appears that the deamidation of hGH was significantly reduced at 37° C. in histidine buffer as compared with phosphate buffer.

Example 2

Reduction of the deamidation in the presence of histidine or histidine derivatives.

The rate of deamidation was examined at 25° C. for hGH preparations comprising 6 IU hGH at pH 6.5 and at pH 7.3 in 5 mm, 10 mM and 100 mM His buffer as compared to 8 mM phosphate buffer at the same pH. Furthermore, the histidine derivatives His—Gly, His—Ala, His—Leu, His—Lys, His—Phe, His—Ser, His methyl ester, histidinol, imidazole, imidazole-4-acetic acid, and histamine were tested.

The hGH preparations were prepared by dissolving 20 mg hGH in 10 ml of histidine buffer of the desired strength prepared by dissolving 7.8 mg, 15.5 mg, and 155.2 mg, respectively, of histidine in 10 ml deionized water containing 0.9% (v/v) of benzyl alcohol and adding 0.1N hydrochloric acid to the stated pH.

The hGH formulations stated in Table 2 were stored at 25° C. and analyzed for the desamido contents after 14 and 30 days by IE-HPLC. The results are shown in Table 2, infra.

TABLE 2

Contents of desamido hGH as determined by IE-HPLC as a function of the formulation and the time in solution at 25° C.:
Formulation (*) Formation of desamido compound at 25° C.

| | 14 days (') | 30 days |
|---|---|---|
| 5 mM His pH 6.5 | 6.5 | 9.1 |
| 5 mM His pH 7.3 | 11.0 | 17.4 |
| 10 mM His pH 6.5 | 6.8 | 9.7 |
| 10 mM His pH 7.3 | 11.3 | 16.6 |
| 100 mM His pH 6.5 | 9.8 | 15.2 |
| 100 mM His pH 7.3 | 19.3 | 28.8 |
| 8 mM di-Na-Phosphate pH 6.5 | 7.8 | 10.8 |
| 8 mM di-Na-Phosphate pH 7.3 | 15.2 | 20.3 |
| 8 mM di-Na-phosphate pH 6.5, 0.3% m-cresol | 9.4 | 13.2 |
| 10 mM Asp, pH 6.5 | 21.7 | nd |
| 10 mM Glu, pH 6.5 | 14.8 | nd |
| 10 mM His-Gly, pH 6.2 | 5.6 | 8.1 |
| 10 mM His-Ala pH 6.5 | 6.2 | 8.5 |
| 10 mM His-Leu pH 6.5 | 8.8 | 12.3 |
| 10 mM His-Lys pH 6.5 | 8.6 | 12.0 |
| 10 mM His-phe pH 6.5 | 7.5 | 11.3 |
| 10 mM His-Ser pH 6.3 | 22.0 | nd |
| 10 mM His-methyl-ester, pH 6.5 | 4.6 | 5.2 |
| 10 mM histidinol pH 6.5 | 27.4 | nd |
| 10 mM imidazole pH 6.5 | 9.2 | 12.2 |
| 10 mM imidazole-4-acetic acid pH 6.5 | 10.3 | 14.2 |
| 10 mM Histamine pH 6.5 | 9.8 | 12.2 |

*Comprises 0.9% benzyl alcohol, except formulation No. 9
The contents of desamido-hGH in the starting material was 2.1%.

From the above Table 2, it appears that the deamidation of hGH was reduced by approximately 20% by the addition of histidine as compared with phosphate buffer at pH 6.5 and 7.3. Furthermore, a reduction of the pH from 7.3 being the conventional pH of commercial hGH preparations to 6.5 in itself gives rise to a reduction of the rate of de-amidation by 50%.

Histidinol does not seem to stabilize the preparations under the test conditions, and addition of histidine in larger amounts does not add but rather detracts from the desired effect.

Comparable results were obtained using histidine analogs such as imidazole, histamine, and imidazole-4-acetic acid as well as the histidine methyl ester, giving rise to the formation of only 3.1% desamido-hGH after 30 days at 25° C., allowing for a lifetime of the preparation of 3–4 months.

Addition of Asp or Glu increased the rate of deamidation as compare to phosphate at pH 6.5.

Addition of dipeptides of the type His-X showed a positive effect for His—Gly and His—Ala, whereas His—Ser reduced the stability to deamidation.

The above results show that the rate of deamidation is reduced by lowering the pH and by adding histidine in a low concentration, preferably about 5 mM–10 mM. The rate of deamidation may be reduced by more than 50% by lowering the pH and substituting the phosphate buffer with histidine. The use of m-cresol or benzyl alcohol as preservatives seemed to have no influence on the rate of deamidation.

Split-formation (hydrolysis of peptide bonds) is reduced by histidine at pH 6.5 in comparison with phosphate.

Example 3

Reduction of the formation of sulfoxide.

The dependency of the pH and the type of buffer was examined.

Dependency of pH:

Formulation:

A commercial hGH preparation (Norditropin®, 12 IU/ml) comprising bicarbonate, glycine and mannitol+0.9% benzyl alcohol was adjusted to pH 8.3, 8.0, 7.5, 7.0, 6.5 and 6.0 using 0.1N hydrochloric acid, and the samples were left at 37° C. Analysis was carried out by RP-HPLC after 0, 7 and 14 days. The results are shown in Table 3, infra.

TABLE 3

| | Formation of Sulfoxide | | |
|---|---|---|---|
| Sample | Temp °C. | Days % | Sulfoxide |
| pH 8.37 | — | 0 | 1.0 |
| pH 8.37 | 37 | 7 | 9.0 |
| pH 8.04 | 37 | 7 | 8.7 |
| pH 7.52 | 37 | 7 | 8.3 |
| pH 7.01 | 37 | 7 | 7.7 |
| pH 6.52 | 37 | 7 | 6.5 |
| pH 6.02 | 37 | 7 | 4.8 |
| pH 8.37 | 37 | 14 | 14.9 |
| pH 8.04 | 37 | 14 | 14.5 |
| pH 7.52 | 37 | 14 | 14.0 |
| pH 7.01 | 37 | 14 | 12.9 |
| pH 6.52 | 37 | 14 | 11.1 |
| pH 6.02 | 37 | 14 | 7.7 |

The formation of sulfoxide of hGH was reduced when lowering the pH from 8.4 to 6.0.

Type of Buffer, pH:

A B-hGH preparation comprising 12 mg/ml distilled water was diluted in the proportion 1+10 with various buffers in a concentration of 15 mM and optional added further additive(s). The samples were left at 25° C., and analysis by RP-HPLC was carried out after 10 and 34 days. The results of the RP-HPLC and optional additives are shown in Table 4, infra.

TABLE 4

Formation of Sulfoxide

| | | | Sulfoxidated | |
|---|---|---|---|---|
| Buffer | pH | Additive | 10d % | 34d |
| Phosphate | 7.3 | — | 1.9 | 5.5 |
| Histidine | 7.3 | — | 0.9 | 2.4 |
| Histidine | 6.9 | — | 0.9 | 2.0 |
| Histidine | 6.5 | — | 0.8 | 1.9 |
| Histidine | 7.3 | 18 mM Met | 0.8 | 2.0 |
| Histidine | 7.3 | 18 mM Cys | 2.4 | 2.9 |
| Histidine | 7.3 | 0.42 mM toc. | 1.1 | 3.0 |
| Histidine | 7.3. | 9% ethanol | 1.3 | 4.2 |
| Histidine | 7.3 | 18 mM asc. | 41 | nd |
| Histidine | 7.3 | 0.8% NaCl | 1.3 | 3.5 |

Toc.: tocoferol; asc.: ascorbic acid.

As compared with phosphate buffer, a marked reduction of the formation of sulfoxidated B-hGH is observed in histidine buffer (pH 7.3). A reduction of the formation of sulfoxide is observed with falling pH in His-buffer.

No further effect was obtained by addition of anti-oxidants or other additives.

Example 4
Crystallization of hGH in the presence of phosphate or histidine buffer Aliquots of a hGH solution prepared according to Dal-boege et al., 1987, Biotechnology 5:161–164, in concentrations of 6 mg/ml were incubated in 10 mM phosphate or 10 mM histidine buffer at pH 6.2. To each of the samples was added ethanol to a final concentration of 7.5% (v/v) followed by addition of zinc acetate solution to a final zinc concentration of 1.34 mol Zn/mol hGH in the case of phosphate buffer and 5.5 mol Zn/mol hGH in the case of histidine buffer.

Figure 2:
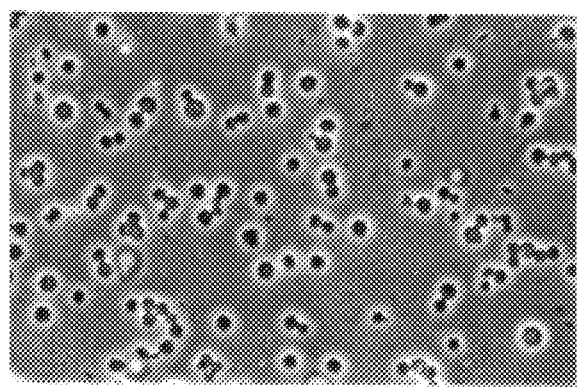
FIG. 2 shows a photo of crystals of hGH according to the invention, specifically in the presence of histidine buffer. Magnification: 400×.

The crystals were grown in suspension for 16 hrs. and the crystallization was monitored by phase contrast microscopy. The crystals formed in histidine buffer have a well defined unisized hexagonal appearance comprising little or no amorphous contaminants (FIG. 2). On the contrary, hGH crystals formed in phosphate buffer under the exact identical conditions showed a much more pronounced heterogenous appearance comprising a considerable amount of amorphous material (FIG. 1).

The crystals were allowed to grow for a further 5 days. Crystals formed in both histidine and phosphate buffer were collected by centrifugation and the crystals were dissolved in 7M urea followed by hGH analysis.

| Buffer | % crystals | % free hGH |
|---|---|---|
| Histidine | 65 | 35 |
| Phosphate | 55 | 45 |

Thus histidine buffer was found to provide better conditions for hGH crystallization with respect to both yield of crystals and quality.

Example 5

The stability of lyophilized hGH preparations comprising histidine and sucrose or mannitol compared to a conventional hGH preparation containing phosphate, glycine and mannitol.

The following preparations 1–8 were made by desalting a hGH solution into the stated histidine buffers. After adjusting the hGH concentration to 6 IU/ml with the various histidine buffers, the stated amounts of mannitol and sucrose were dissolved. Preparation 9 corresponds to a conventional hGH preparation and was used as reference.

All hGH solutions 1–9 were filled into vials a 1 ml and lyophilized.

Analyses of hGH were performed after reconstitution with a 0.9% solution of benzyl alcohol.

1. hGH 6 IU/ml
  Adjusted to pH 6.5 using HCl
  Mannitol 33 mg/ml
2. hGH 6 IU/ml
  Adjusted to pH 6.5 using HCl
  Sucrose 62 mg/ml
3. hGH 6 IU/ml
  Adjusted to pH 7.0 using HCl
  Mannitol 33 mg/ml
4. hGH 6 IU/ml
  Adjusted to pH 7.0 using HCl
  Sucrose 62 mg/ml
5. hGH 6 IU/ml
  Adjusted to pH 6.5 using HCl
  Mannitol 33 mg/ml
6. hGH 6 IU/ml
  Adjusted to pH 6.5 using HCl
  Sucrose 62 mg/ml
7. hGH 6 IU/ml
  Adjusted to pH 7.0 using HCl
  Mannitol 33 mg/ml
8. hGH 6 IU/ml
  Adjusted to pH 7.0 using HCl
  Sucrose 62 mg/ml
9. hGH 6 IU/ml
  $Na_2HPO_4, 2H_2O$ 0.59 mg/ml
  $NaH_2PO_4, 2H_2O$ 0.53 mg/ml
  Mannitol, 20.5 mg/ml
  Adjusted to pH 7.0 using phosphoric acid The lyophilized products are readily soluble and forms clear aqueous solutions.

The amount of polymer before lyophilization (BL) and immediately after lyophilization, after 7 months at 4° C., after 7 months at 4° C. plus 4 months at 37° C. and after 7 months at 4° C. plus 4 months at 25° C. in % is stated in Table 5. The amount of dimer in % is stated in Table 6.

The amount of desamido hGH in % is stated in Table 7, and The amount of sulfoxide in % is stated in Table 8.

The amount of desamido hGH and sulfoxide was determined as in Examples 1–4.

The amount of dimer and polymer was determined by gp-HPLC.

TABLE 5

| | | | Amount of Polymer in % | | |
|---|---|---|---|---|---|
| Buffer | BL | T = 0 | 7 mos. 4° C. | 7 mos. 4° C. + 4 mos. 37° C. | 7 mos. 4° C. + 4 mos. 25° C. |
| No. 1 | 0.2 | 1.5 1.5 | 2.0 | 6.0 | — |
| No. 2 | — | 0.2 0.2 | 0.2 | 0.2 | 0.2 |
| No. 3 | 0.2 | 0.8 1.0 | 1.8 | 4.0 | 2.6 |
| No. 4 | — | 0.2 <0.2 | 0.2 | <0.2 | <0.2 |

TABLE 5-continued

| | | | Amount of Polymer in % | | |
|---|---|---|---|---|---|
| Buffer | BL | T = 0 | 7 mos. 4° C. | 7 mos. 4° C. + 4 mos. 37° C. | 7 mos. 4° C. + 4 mos. 25° C. |
| No. 5 | <0.2 | 0.8 0.7 | 1.6 | 3.1 | 3.0 |
| No. 6 | — | 0.2 0.2 | 0.2 | 0.2 | <0.2 |
| No. 7 | 0.2 | 1.3 1.4 | 2.0 | 3.1 | 2.3 |
| No. 8 | — | 0.2 0.2 | 0.2 | <0.2 | <0.2 |
| No. 9 | 0.2 | 1.2 1.4 | 2.3 | 2.9 | 2.2 |

The amount of polymer is clearly lower for samples comprising sucrose.

TABLE 6

| | | | Amount of Dimer in % | | |
|---|---|---|---|---|---|
| Buffer | BL | T = 0 | 7 mos. 4° C. | 7 mos. 4° C. + 4 mos. 37° C. | 7 mos. 4° C. + 4 mos. 25° C. |
| No. 1 | 0.4 | 0.8 0.9 | 1.8 | 3.6 | — |
| No. 2 | — | 0.4 0.4 | 0.3 | 2.8 | 0.4 |
| No. 3 | 0.4 | 1.1 1.1 | 2.2 | 5.6 | 4.7 |
| No. 4 | — | 0.4 0.4 | 0.4 | 3.3 | 0.4 |
| No. 5 | 0.3 | 0.6 0.6 | 1.1 | 3.4 | 2.2 |
| No. 6 | — | 0.4 0.4 | 0.3 | 3.1 | 0.3 |
| No. 7 | 0.3 | 0.9 0.9 | 1.4 | 4.7 | 3.3 |
| No. 8 | — | 0.4 0.5 | 0.4 | 3.0 | 0.4 |
| No. 9 | 0.5 | 0.6 0.7 | 1.0 | 4.3 | 2.2 |

The amount of diner is clearly lower for samples comprising sucrose.

TABLE 7

| | | | Amount of Desamido hGH in % | | |
|---|---|---|---|---|---|
| Buffer | BL | T = 0 | 7 mos. 4° C. | 7 mos. 4° C. + 4 mos. 37° C. | 7 mos. 4° C. + 4 mos. 25° C. |
| No. 1 | 2.0 | 1.8 1.4 | 1.1 | 3.9 | — |
| No. 2 | — | 1.4 1.5 | 3.1 | 22.8 | 1.3 |
| No. 3 | 2.1 | 1.2 1.3 | 2.1 | 5.6 | 1.5 |
| No. 4 | — | 1.6 1.6 | 2.1 | 23.6 | 1.0 |
| No. 5 | 1.6 | 1.3 0.9 | 1.4 | 12.1 | 1.0 |
| No. 6 | — | 1.2 1.3 | 1.6 | 23.0 | 1.4 |
| No. 7 | 2.0 | 1.4 1.6 | 1.0 | 4.8 | 4.6 |
| No. 8 | — | 1.5 1.4 | 1.9 | 20.2 | 2.9 |
| No. 9 | 2.1 | 1.7 1.5 | 2.0 | 9.9 | 3.6 |

The amount of desamido-hGH is very low for compositions comprising histidine after 7 months at 4° C.+4 months at 25° C.

TABLE 8

| Buffer | Amt. of Desamido hGH in % |
|---|---|
| No. 1 | — |
| No. 2 | 1.0 |
| No. 3 | 4.8 |
| No. 4 | 1.1 |
| No. 5 | — |
| No. 6 | 1.0 |
| No. 7 | 1.8 |
| No. 8 | 1.4 |
| No. 9 | 2.4 |

*7 mos. 4° C. + 4 mos. 25° C.

The amount of sulfoxide was clearly lower in samples comprising sucrose.

Example 6

Stability of lyophilized preparations comprising histidine, mannitol and disaccharide.

The following preparations were made in the same manner as disclosed in Example 5.

10. hGH 6 IU/ml

Adjusted to pH 6.5 using HCl

Sucrose 21 mg/ml

Mannitol 22 mg/ml 11. hGH 6 IU/ml

Adjusted to pH 7.0 using HCl

Sucrose 21 mg/ml

Mannitol 22 mg/ml 12. hGH 6 IU/ml

Adjusted to pH 7.0 using HCl

Trehalose 20 mg/ml

Mannitol 22 mg/ml

The amount of desamido-hGH, polymer, and dimer in % was determined before lyophilization (BL), at t=0, after three months at 40° C. and after 6 months at 25° C. The results are shown below in Tables 9–11.

It appears that samples comprising mannitol and sucrose or trehalose show better stability than samples comprising only mannitol as bulking agent for the lyophilization.

TABLE 9

| | Amount of Desamido-hGH in % | | | |
|---|---|---|---|---|
| Buffer | BL | T = 0 | 3 mos. at 40° C. | 6 mos. at 25° C. |
| No. 1 | | 0.8 | 3.0 | 3.1 |
| No. 10 | 1.3 | 0.9 | 1.7 | 2.4 |
| No. 3 | | 0.9 | 2.4 | 3.0 |
| No. 11 | 0.9 | 1.4 | 1.2 | 2.0 |
| No. 12 | | 1.0 | 1.8 | 1.9 |
| No. 9 | 0.7 | 0.7 | 2.5 | 3.4 |

TABLE 10

| | Amount of Polymer in % | | | |
|---|---|---|---|---|
| Buffer | BL | T = 0 | 3 mos. at 40° C. | 6 mos. at 25° C. |
| No. 1 | | 1.1 | 5.0 | 4.1 |
| No. 10 | 0.4 | 0.6 | 1.8 | 1.3 |
| No. 3 | | 0.9 | 5.2 | 3.2 |

TABLE 10-continued

| | Amount of Polymer in % | | | |
|---|---|---|---|---|
| Buffer | BL | T = 0 | 3 mos. at 40° C. | 6 mos. at 25° C. |
| No. 11 | 0.5 | 0.6 | 1.5 | 1.1 |
| No. 12 | | 0.8 | 1.3 | 1.1 |
| No. 9 | 0.4 | 0.6 | 1.9 | 1.6 |

TABLE 11

| | Amount of Dimer in % | | | |
|---|---|---|---|---|
| Buffer | BL | T = 0 | 3 mos. at 40° C. | 6 mos. at 25° C. |
| No. 1 | | 1.3 | 4.3 | 3.8 |
| No. 10 | 0.5 | 0.9 | 1.8 | 1.6 |
| No. 3 | | 1.3 | 5.0 | 4.3 |
| No. 11 | 0.6 | 1.2 | 2.2 | 1.8 |
| No. 12 | | 1.1 | 1.6 | 1.4 |
| No. 9 | 0.6 | 0.9 | 1.0 | 2.3 |

Example 7

Formulation of a pharmaceutical preparation containing crystals of hGH:

Crystals were grown as described in Example 4 and stored at 4° C. The crystals were then isolated by centrifugation and subsequent removal of the mother liquor. Then the crystals were lyophilized overnight to achieve dry crystals without remaining organic solvent. A pharmaceutical suspension of the dried crystals was prepared according to the following formulation:

hGH crystals 1.3 mg/ml
Histidine 1.6 mg/ml
$Zn(Ac)_2,H_2O$ 0.1 mg/ml
Benzyl alcohol 0.9% (v/v)
The pH was adjusted to 6.5 using HCl.

Example 8

Example 7 was repeated with the exception that $Zn(Ac)_2,H_2O$ was omitted, giving a suspension of the following formulation:

hGH crystals 1.3 mg/ml
Histidine 1.6 mg/ml
Benzyl alcohol 0.9% (v/v)
The pH was adjusted to 6.2.

Example 9

The crystals were treated in the same way as in Example 7 and the following suspension was formulated:

hGH crystals 1.3 mg/ml
Histidine 1.33 mg/ml
NaCl 5.7 mg/ml
Benzyl alcohol 0.9% (v/v)
The pH was adjusted to 6.2.

Example 10

The crystals were treated in the same way as in Example 7 and the following solution was prepared:

hGH crystals 1.3 mg/ml
Histidine 1.14 mg/ml
NaCl 9.0 mg/ml
The pH was adjusted to 6.1.

Example 11

In an analogous manner as described in Example 1 biosynthetic human growth hormone was formulated in a concentration of 6 IU/ml in 0.9% benzyl alcohol at pH 6.5 in various concentrations of histidine, 0, 1, 2, 5, 10, 20, 30, 50, or 100 mM.

The samples were stored 7 days at 37° C. and analyses for the contents of desamido, oxidized forms and dimers and polymers were performed in the same manner as described above. The results are shown in Table 12, infra wherein the contents of desamido-hGH, dimers and polymers, and oxidized forms are determined by IE-HPLC, GP-HPLC and RP-HPLC and the contents of the cleaved forms of hGH is measured by IE-HPLC.

The amount of dimer is low when the concentration is 1 mM histidine or above, for formation of desamido compounds concentrations of histidine of up to 30 mM gives acceptable results, and for formation of oxidized forms concentrations of histidine below 20 mM are preferred. An overall optimum is seen for a concentration of histidine of 5 mM.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A pharmaceutical composition in the form of a lyophilized powder comprising a growth hormone or a derivative thereof and histidine or histidine derivative, in which said derivative is selected from the group consisting of an amide or ester of histidine, imidazole, imidazole-4-acetic acid, des-amino-His, His—Leu, His—Ala, His—Lys, and His—Phe, in an amount of from about 0.1 to about 12 mg histidine per mg of growth hormone or a derivative thereof.

2. A pharmaceutical composition in the form of a buffered aqueous solution comprising a growth hormone or derivative thereof buffered with histidine or histidine derivative, in which said derivative is selected from the group consisting of an amide or ester of histidine, imidazole, imidazole-4-acetic acid, des-amino-His, His—Leu, His—Ala, His—Lys, and His—Phe at a concentration from about 1 mM to about 100 mM.

3. The pharmaceutical composition of claim 2 in which said composition has a pH from about 2 to about 8.

4. The pharmaceutical composition of claim 3 in which said composition has a pH from about 5 to about 7.

5. The pharmaceutical composition of claim 3 in which said composition has a pH of about 6.8.

6. The pharmaceutical composition of claim 2 in which the solution is buffered with histidine or derivative thereof at a concentration from about 1 mM to about 10 mM.

7. The pharmaceutical composition of claim 2 in which the solution is buffered with histidine or derivative thereof at a concentration from about 2 mM to about 6 mM.

8. The pharmaceutical composition of claim 2 in which the solution is buffered with histidine or derivative thereof at a concentration from about 3 mM to about 5 mM.

9. The pharmaceutical composition of claim 2 in which said composition further comprises a sugar alcohol or a disaccharide or a mixture thereof.

10. The pharmaceutical composition of claim 9 in which the sugar alcohol is mannitol.

11. The pharmaceutical composition of claim 9 wherein the disaccharide is sucrose or trehalose.

12. The pharmaceutical composition of claim 1 wherein the growth hormone is human growth hormone.

13. The pharmaceutical composition of claim 2 wherein the growth hormone is human growth hormone.

14. Crystalline growth hormone or a derivative thereof comprising histidine or histidine derivative, in which said derivative is selected from the group consisting of an amide or ester of histidine, imidazole, imidazole-4-acetic acid, des-amino-His, His—Leu, His—Ala, His—Lys, and His—Phe and a cation.

15. The crystalline growth hormone of claim 14 wherein the growth hormone is human growth hormone.

16. A method of preparing the crystalline growth hormone of claim 14 comprising the steps of:
  a) forming a solution of growth hormone or a growth hormone derivative in a solvent and adding histidine or histidine derivative, in which said derivative is selected from the group consisting of an amide or ester of histidine, imidazole, imidazole-4-acetic acid, des-amino-His, His—Leu, His—Ala, His—Lys, and His—Phe using hydrochloric acid;
  b) adding organic or inorganic cations to the solution of step (a);
  c) crystallizing the solution of step (b) at a temperature from about 0° C. to about 30° C.; and
  d) isolating the crystals formed in step (c).

17. The method of claim 16 wherein the solvent in step (a) is selected from the group consisting of short chained aliphatic, alicyclic or aromatic alcohols and ketones.

18. The method of claim 16 in which the solution of step (a) is adjusted to a pH from about 5 to about 8.

19. A method for treating a disorder in a patient affectable by growth hormone comprising treating the patient with an amount of the composition of claim 1 effective to treat said disorder.

20. A method for treating a disorder in a patient affectable by growth hormone comprising treating the patient with an amount of the composition of claim 2 effective to treat said disorder.

21. A method for treating a disorder in a patient affectable by growth hormone comprising treating the patient with an amount of the composition of claim 16 effective to treat said disorder.

* * * * *